(12) United States Patent
Udding et al.

(10) Patent No.: US 7,160,951 B2
(45) Date of Patent: Jan. 9, 2007

(54) PEROXIDE COMPOSITIONS WITH REACTIVE DILUENTS

(75) Inventors: Jan H Udding, Zwolle (NL); Agnes E Wolters, Laag Zuthem (NL); Heinz Wilhelm, Hassloch (DE); Armin Pfeil, Kaufering (DE); Thomas Bürgel, Landsberg (DE); Lutz Sager, Scheuring (DE)

(73) Assignees: DSM IP Assets B.V., Te Heerlen (NL); Hilti Aktiengesellschaft (LI)

( * ) Notice: Subject to any disclaimer, the term of this patent is extended or adjusted under 35 U.S.C. 154(b) by 271 days.

(21) Appl. No.: 10/451,049

(22) PCT Filed: Dec. 19, 2001

(86) PCT No.: PCT/NL01/00922

§ 371 (c)(1),
(2), (4) Date: Dec. 8, 2003

(87) PCT Pub. No.: WO02/051879

PCT Pub. Date: Jul. 4, 2002

(65) Prior Publication Data

US 2004/0094744 A1    May 20, 2004

(30) Foreign Application Priority Data

Dec. 22, 2000  (EP) ................... 00204745

(51) Int. Cl.
*C08F 261/06* (2006.01)
(52) U.S. Cl. ................ 525/263; 525/312; 525/332
(58) Field of Classification Search ............... 525/263, 525/312; 526/332
See application file for complete search history.

(56) References Cited

U.S. PATENT DOCUMENTS

| | | | |
|---|---|---|---|
| 3,721,722 A | | 3/1973 | Baum |
| 3,876,726 A | | 4/1975 | Ford, Jr. et al. |
| 4,100,225 A | * | 7/1978 | Mueller ............. 525/276 |
| 4,130,501 A | | 12/1978 | Lutz et al. |
| 4,742,120 A | * | 5/1988 | Higaki et al. ........ 525/276 |
| 4,944,819 A | | 7/1990 | Gebauer |
| 5,157,072 A | | 10/1992 | Hense et al. |
| 5,470,897 A | | 11/1995 | Meixner et al. |
| 6,054,502 A | | 4/2000 | Friedlander et al. |
| 2004/0068044 A1 | | 4/2004 | Udding et al. |
| 2004/0072954 A1 | | 4/2004 | Udding et al. |
| 2004/0094744 A1 | | 5/2004 | Udding et al. |

FOREIGN PATENT DOCUMENTS

| | | |
|---|---|---|
| DE | 32 26 602 | 1/1984 |
| DE | 39 40 138 | 6/1991 |
| DE | 42 31 161 | 3/1994 |
| EP | 0 028 841 | 5/1981 |
| EP | 0 322 808 | 7/1989 |
| EP | 0 432 087 | 6/1991 |
| EP | 0 534 197 | 3/1993 |
| EP | 0 534 201 | 3/1993 |
| EP | 0 591 803 | 4/1994 |
| GB | 915 009 | 1/1963 |
| JP | 09-059329 | 3/1997 |
| WO | 94/19397 | 9/1994 |
| WO | 99/54403 | 10/1999 |
| WO | 00/08081 | 2/2000 |
| WO | WO 00 09478 | 2/2000 |
| WO | 00/78833 | 12/2000 |

OTHER PUBLICATIONS

Derwent Publication, vol. 19, No. 97, "Curable resin composition with rapid curability for sealant or adhesive—comprises . . ."; Documentation Abstracts Journal A. Plastics.
Derwent Publication, vol. 368, No. 46, "Use of vinyl ether as comonomer for unsaturated polyester resins—in peroxide cure systems as a non-carcinogenic substitute for styrene comonomers"; Dec. 10, 1994.

* cited by examiner

*Primary Examiner*—Bernard Lipman
(74) *Attorney, Agent, or Firm*—Nixon & Vanderhye, P.C.

(57) ABSTRACT

The invention relates to peroxide compositions comprising a reactive diluent for the peroxide, wherein the diluent is either a component containing one or more vinyl ether group(s) and having a monomeric structure according to formula 1, $(A-CH=CH-O)_n-R$, or is a suitable resinous compound comprising, in a covalently built-in manner, a component containing one or more vinyl ether group(s). In the formula
A represents hydrogen or an alkyl group with 1–3 C atoms, and individual A groups may be different
R either represents an aliphatic group, optionally branched, with 1–20 C atoms, etc.
or represents a polyethylene or polypropylene glycol with 2 to 120 glycol units, etc. and
n is 1, 2, 3 or 4.

The resinous compounds comprising, in a covalently built-in manner, a component containing one or more vinyl ether group(s)are obtained by reaction of:
a) a first compound (the HVE-compound) containing at least one hydroxyl group and at least one vinyl ether group, and
b) a second compound (the D/HIC-compound), being an isocyanate, reacting with formation of one or more urethane group(s), and
c) a third compound (the G/P/HP-compound) chosen from the groups of (1) $C_{2-6}$ glycols, (2) $C_{5-20}$ polyols having 2–5 hydroxyl groups and (3) hydroxyl terminated polyester compounds, not being alkyd resins, having 1–5 free hydroxyl groups and from 2–50 monomeric ester units (the G/P/HP-compound), or mixtures thereof.

The invention also relates to the preparation of such compositions and to the use of such reactive diluents for peroxides in radically curing of unsaturated polyester resins for structural applications.

14 Claims, No Drawings

PEROXIDE COMPOSITIONS WITH REACTIVE DILUENTS

CROSS REFERENCE TO RELATED APPLICATION

This application is the National Phase of International Application PCT/NL01/00922 filed Dec. 19, 2001 which designated the U.S., and that International Application was published under PCT Article 21(2) in English.

The present invention relates to peroxide compositions comprising (a new class of) reactive diluents for the peroxide. The present invention also relates to the preparation of such peroxide compositions and to the use of (said new class of) reactive diluents for peroxides in processes for radically curing of—optionally reinforced—unsaturated polyester resins for structural applications. The invention finally relates to products obtained by curing with a peroxide composition according to the present invention.

Diluents for peroxides are compounds or compositions, which are being used for enabling the peroxides to be suitably stored and handled, as free flowing or pumpable products, before they are being used in chemical reactions. Referring to their function, namely of making the composition free flowing or pumpable, such compounds or compositions also may be called "flow enhancers" or "extenders". Two main categories of diluents can be distinguished, non-reactive diluents and reactive diluents. In general diluents do not need to be reactive (further definition is given below) to be suitable as a diluent.

Non-reactive types of diluents generally are also being referred to as phlegmatizers: this is, because they ensure that any unwanted reactions of peroxides do not start before the peroxide composition (diluent plus peroxide) is added to the reaction system of the chemical reaction. This ensures easy and safe handling of peroxides. Until now many compounds and compositions have been described as being suitable phlegmatizers for peroxides. An industrially important class of chemical reactions where peroxides are involved is formed by the processing (curing, for instance for making laminates or for chemical fastening) of unsaturated polyester resins (or vinyl ester resins, vinyl urethane resins or hybrid resins; hybrid resins as meant herein are mixtures of vinyl ester or unsaturated polyester resins with isocyanates) dissolved in a suitable monomer. For such curing reactions usually phlegmatized peroxides are used in order to initiate polymerization by radical reaction.

Reactive diluents, on the other hand, are chemical compounds, which do not readily react with peroxides as such, but are able to react in the presence of (and with) a radically curable resin, for instance an unsaturated polyester. In the peroxide composition, however, the reactive diluent also has a phlegmatizing function. The present invention also relates to methods for preparing the new class of peroxide compositions and to the use of (such new class of) reactive diluents for peroxides in processes for curing of unsaturated polyester resins, and the like.

Peroxide compositions comprising a (liquefying, non-reactive) diluent, for instance phthalate diluents or extenders, are well known as commercially available state-of-the-art products; for instance, so-called BP-pastes from AKZO Nobel. Examples are Lucidol BT 50™ and Lucidol BK 50™. In the patent literature also various examples of the use of such extended peroxide compositions can be found; for instance, see DE-3226602-A1 and EP-A-0432087. Percarbonates, for instance, are commercially available as powdery products. Since in the phlegmatized peroxide compositions of the prior art a relatively high amount of phlegmatizer is used relative to the peroxide (a typical ratio of phlegmatizer to peroxide is about 4:5), only small quantities of the peroxide compositions can be used in order to avoid that the properties of the finally cured products are negatively affected by too high phlegmatizer contents. Generally it will be necessary to limit the content of phlegmatizer in the finished product, even though the process conditions and/or the employed machinery in the curing step would call for the addition of higher amounts of the peroxide composition.

In general, when additional quantities of phlegmatizers cannot be used for whatever reason, further often problems of improper mixing can be observed. Poor mixing results in poor curing and thus gives inadequate behaviour and/or properties of the finished articles obtained after the curing.

The skilled man, until now, always is looking for a balance between the amount of peroxide (composition with phlegmatizer) to be used in the curing and the achievable mechanical properties of the final cured products. In particular, in case really a high amount of peroxide is needed for the curing, this is even more critical. Such peroxide then often even must be diluted with additional quantities of phlegmatizer, because otherwise homogeneous mixing of the peroxide composition and the unsaturated polyester is not likely to be achieved within an acceptable time frame. Such additional amounts of phlegmatizer inevitably lead to impaired mechanical properties in the final product. It also may be the case that the use of such additional amounts of phlegmatizer for diluting the peroxide composition is not allowed or undesirable in view of existing legislation and/or other approvals, for instance with regard to possible contact of finished articles with food and/or drinking water. For such reasons the use of phthalates as diluent for peroxides is certainly not preferred, but so far no good alternative(s) have been available.

To overcome the above disadvantages of the diluents or phlegmatizers of the prior art one has attempted in the past to use reactive diluents instead of the (aforementioned) non-reactive phlegmatizers such as phthalates.

Reactive phlegmatizers have been discussed several times in the prior art. For instance, the extending of peroxides with reactive carriers containing isocyanate or epoxy groups is described in DE-A-4304824 and WO-94/19397. The peroxide compositions according to said reference are very sensitive for moisture and any moisture taken up results, in the ultimate curing processes, in undesired foaming phenomena and is accompanied by irregular building-in of the diluent used. This strongly affects the properties of the final cured products obtained therewith. To overcome part of the problems when using such reactive diluents, for instance in the production of glass-fibre laminates made of unsaturated polyesters, the skilled man used to lower the concentration of peroxide added to the polyester and necessarily had to accept longer handling times during the curing for achieving acceptable properties of the final cured products.

Moreover, in most of the cases the potential use of reactive diluents was only quite limited, because in general they only could be used when the peroxide composition was to be used for a reaction within a few days from preparation of the peroxide composition. Longer storage times than a few days, without substantial curing or gelling of the reactive diluent, so far have not been reported for peroxide compositions with reactive diluents, whereas with non-reactive diluents acceptable storage-times in the order of some weeks to some months can be achieved. It is evident that peroxide compositions having no more than a few days of acceptable storage time under ambient conditions are quite unsuitable for most practical applications thereof.

Thus, there is a long-felt need for, possibly highly diluted, peroxide compositions, which are stable under ambient conditions for at least a few weeks, preferably about as long as are obtainable with non-reactive diluents or even better, and which are easy to handle (e.g. by pouring and/or pumping) without resulting in any of the above problems during the final curing processes.

Surprisingly these goals of obtaining pumpable, possibly highly diluted, storage-stable peroxide compositions were reached in that the inventors now have provided peroxide compositions comprising (a new class of) reactive diluents for peroxides wherein the diluent is either a component containing one or more vinyl ether group(s) and having a (monomeric) structure according to formula 1

(A—CH=CH—O)$_n$—R     (formula 1)

where

A represents hydrogen or an alkyl group with 1–3 C atoms, and where, if there is more than one A, the individual A groups may be the same or different R either represents an aliphatic group, optionally branched, with 1–20 C atoms, which may also contain a cyclohexyl or a 1,4-dimethylenecyclohexyl group and in the carbon chain optionally also one or more O and/or S atoms, which group may be substituted with one or more functional group(s) chosen from either a hydroxyl group or an amino group, optionally substituted with one or two alkyl groups with 1–3 C atoms, or represents a polyethylene glycol or a polypropylene glycol with an average chain length of between 2 and 120 glycol units, optionally with an aliphatic group with 1–5 C atoms attached to the chain's free hydroxyl group and n is 1, 2, 3 or 4, or is a suitable resinous compound comprising, in a covalently built-in manner, a component containing one or more vinyl ether group(s). The inventors have found that these components, whether being used as monomers or covalently built-in into a suitable resinous compound, are stable in the presence of peroxides if no other reactive, i.e. co-polymerizable, materials are present.

The monomeric components with one or more vinyl ether group(s), which suitably can be used as a diluent in the present invention, are commercially available.

Suitable examples of components according to formula 1 are given further below. At this place it may suffice to mention, that the vinyl ether monomers are preferably mono- or divinyl ether monomers. Most preferably, the vinyl ether monomer is hydroxybutyl vinyl ether (HBUVE), diethyleneglycol divinyl ether (DEGDVE) or triethyleneglycol divinyl ether (TEGDVE).

Also resinous compounds comprising, in a covalently built-in manner, a component containing one or more vinyl ether group(s) can suitably be used as an diluent in the present invention. These are resinous components with one or more vinyl ether group(s) obtained by reaction of a mixture of appropriate amounts of:

a) a first compound (the HVE-compound) containing at least one hydroxyl group and at least one vinyl ether group, and b) a second compound (the D/HIC-compound), being a diisocyanate (or higher isocyanate), reacting with formation of one or more urethane group(s), and c) a third compound (the G/P/HP-compound) chosen from the groups of (1) $C_{2-6}$ glycols, (2) $C_{5-20}$ polyols having 2–5 hydroxyl groups and (3) saturated or (ethylenically) unsaturated hydroxyl terminated polyester compounds, not being alkyd resins, having 1–5 free hydroxyl groups and from 2–50 monomeric ester units (the G/P/HP-compound), or mixtures thereof.

The HVE-compounds as meant herein form a subclass of the group of monomeric compounds according to formula 1, with the proviso, however, that the HVE-compounds always contain at least one free hydroxyl group and/or amino group. Most preferably, the HVE-compound is hydroxybutyl vinyl ether (HBUVE).

The components containing one or more vinyl ether group(s) as used as diluent for the peroxide compositions according to the invention are able to react (for instance, by cross-linking) with unsaturated polyesters, etc. in the presence of a peroxide (which optionally may be accelerated, e.g. by the presence of amine compounds in the unsaturated polyester).

Other components the reactive diluent is able to react with (in the presence of a peroxide) are monomers from the group of compounds that can react with the ethylenic unsaturation of the unsaturated prepolymer. Examples of such other monomers are vinylaromatic compounds, vinyl esters and vinyl nitriles. Most commonly used are (meth)acrylates, (meth)acrylic acid, and styrene. Examples are: vinyl acetate, vinyl propionate, vinyl versatate, alpha-methyl styrene, p-methyl styrene, vinyl toluene and acrylic or methacrylic (hydroxy)esters of alcohols having 1 to 12 C atoms. It is in the context of the present invention also possible to use such other monomers having more than one unsaturation, for example butanediol di(meth)acrylate, divinyl benzene, diallyl phthalate, triallyl cyanurate or the diallyl and triallyl ethers of trimethylol propane.

As mentioned before, very suitable components to be used as diluent for peroxides can be monomeric components with one or more vinyl ether group(s) according to formula 1, or resinous compounds comprising, in a covalently built-in manner, a component containing one or more vinyl ether group(s) (in which case the HVE-compound again may be a compound according to formula 1, but should contain at least one free hydroxyl and/or amino group).

Examples of vinyl ether monomers according to formula 1, and suitable for being used as a monomeric diluent for peroxides are: 3-aminopropyl vinyl ether, t-amyl vinyl ether, butyl vinyl ether, cyclohexanedimethanol monovinyl ether, cyclohexyl vinyl ether, 3-diethylaminopropyl vinyl ether, diethylene glycol monovinyl ether, dodecyl vinyl ether, ethylene glycol butyl vinyl ether, ethylene glycol monovinyl ether, 2-ethylhexyl vinyl ether, ethyl vinyl ether, hexanediol monovinyl ether, hydroxybutyl vinyl ether, methyl vinyl ether, octadecyl vinyl ether, polyethyleneglycol or polypropylene glycol methyl vinyl ether (varying average molecular weights of the polyethylene glycol are possible, e.g. (only shown for PEG's, but PPG's are similar) PEG-5000, PEG-1500, PEG-1100, PEG-520, PEG-400, PEG-300 or PEG-250; instead of methyl also other lower alkyl ($C_2$ to $C_6$) groups, or a second vinyl group may be present), triethylene glycol methyl vinyl ether; butanediol divinyl ether, cyclohexanedimethanol divinyl ether, diethylene glycol divinyl ether, dipropylene glycol divinyl ether, ethylene glycol divinyl ether, hexanediol divinyl ether, neopentyl glycol divinyl ether, tetraethylene glycol divinyl ether, triethylene glycol divinyl ether, trimethylolpropane trivinyl ether, tripropylene glycol divinyl ether and pentaerythritol tetravinyl ether.

Preferably, the monomeric diluent is a vinyl ether monomer selected from the group of mono- or divinyl ether monomers, for instance: butanediol divinyl ether, butyl vinyl ether, cyclohexanedimethanol divinyl ether, cyclohexanedimethanol monovinyl ether, diethylene glycol divinyl ether, ethylene glycol divinyl ether, 2-ethylhexyl divinyl ether, ethyl vinyl ether, hexanediol divinyl ether, hydroxybutyl vinyl ether, methyl vinyl ether, triethylene glycol divinyl ether, and triethylene glycol methyl vinyl ether.

Most preferably, the vinyl ether monomer is hydroxybutyl vinyl ether (HBUVE), diethyleneglycol divinyl ether (DEGDVE) or triethyleneglycol divinyl ether (TEGDVE).

Examples of HVE-compounds in the resinous component with covalently built-in vinyl ether groups, which suitably can be used as diluent for peroxides are hydroxy vinyl ethers or amino vinyl ethers: 3-aminopropyl vinyl ether, cyclohexanedimethanol monovinyl ether, diethylene glycol monovinyl ether, ethylene glycol monovinyl ether, hexanediol monovinyl ether, hydroxybutyl vinyl ether.

Preferably, the HVE-compound is a selected from the group of hydroxy monovinyl ethers, for instance: cyclohexanedimethanol monovinyl ether, hydroxybutyl vinyl ether. Most preferably, the vinyl ether monomer is hydroxybutyl vinyl ether (HBUVE)

The molecular weight of the vinyl ether monomers usually will be in the range of from 70 to 1000; the molecular weight of the vinyl ether group(s) containing components where the vinyl ether group(s) is/are covalently built-in into a suitable resinous compound will usually be in the range of 500 to 5000; such components having a molecular weight lower, respectively higher than 1500 also may be called oligomers, respectively polymers.

The diisocyanate or higher isocyanate (D/HIC) compound as used in the context of the present invention may be any (linear, branched or cyclic) aliphatic and/or aromatic diisocyanate or higher isocyanate, or prepolymers thereof. Specifically suitable D/HIC compounds are, for instance, toluene diisocyanate (TDI), diphenylmethane diisocyanate (MDI), hexane diisocyanate (HDI), isophoron diisocyanate (IPDI) and isocyanurates.

The G/P/HP-compounds as used in the context of the present invention can suitably be chosen from the groups of (1) $C_{2-6}$ glycols, (2) $C_{5-20}$ polyols having 2–5 hydroxyl groups and (3) saturated or (ethylenically) unsaturated hydroxyl terminated polyester compounds, not being alkyd resins, having 1–5 free hydroxyl groups and from 2–50 monomeric ester units. Suitable glycols, for instance, are (mono-, di- or tri-) ethylene glycol or propylene glycol, 1,4-butanediol, 1,6-hexanediol, 1,4-cyclohexanediol. Suitable $C_{5-20}$ polyols having 2–5 hydroxyl groups, for instance, are pentaerythritol, neopentyl glycol, glycerol, trimethylolpropane, hexanetriol, bisphenol-A and ethoxylated derivatives thereof, sorbitol, 1,4-cyclohexane dimethanol, 1,2-bis(hydroxyethyl)cyclohexane. Suitable saturated or (ethylenically) unsaturated hydroxyl terminated polyester compounds, for instance, are chosen from the group of dihydroxy(meth)acrylates and other (meth)acrylic esters of alcohols having 1–12 C-atoms, 2,2-dimethyl-3-hydroxypropyl-2,2-dimethyl-3-hydroxypropionate, and so on. Alternatively hydroxyl terminated saturated or unsaturated polyester resins can be used; examples are unsaturated polyester (pre)polymers or oligomers, or mixtures thereof. Also mixtures of any of the compounds belonging to the group of G/P/HP-compounds can suitably be used.

The molar ratio of (HVE-compound): (D/HIC-compound): (G/P/HP-compound) as used in the context of the present invention is chosen to be approximately 2:2:1. By reacting the HVE-, D/HIC- and G/P/HP-compounds in about said ratio resins are obtained containing at least one vinyl ether group and at least two urethane groups.

In a preferred embodiment of the present invention, the resinous compound comprising, in a covalently built-in manner, a component containing one or more vinyl ether group(s) is obtained from a reaction mixture wherein the first component is formed by a mixture of an HVE-compound and a hydroxylated (meth)acrylate (HA) compound. Suitable HA-compounds as can be used in the present invention are hydroxyethyl acrylate (HEA), hydroxyethyl methacrylate (HEMA) and hydroxypropyl methacrylate (HPMA).

For the reactions between the HVE-compound (and optionally the HA-compound), the D/HIC-compound and the G/P/HP-compound as necessary for the structural incorporation of the component with one or more vinyl ether group(s) into the resin, reaction conditions can be used as are well-known to the skilled man from the synthesis of vinyl ester resins or vinyl ester urethane resins, hereinafter referred to. Examples of suitable methods are described in the experimental part hereof. In addition reference is made to general literature such as "Chemistry and Technology of Isocyanates", H. Ulrich, Wiley & Sons, ISBN 0-471-96371-2, pages 347–403.

Of course, also a mixture of two or more components containing one or more vinyl ether group(s) can be used in the peroxide compositions according to the invention. In case resinous compounds comprising, in a covalently built-in manner, a component containing one or more vinyl ether group(s) are being used, it may be advantageous that such resinous compounds carry one or more additional substituent groups, or in other words are modified by suitable chemical backbones or end groups, in order to achieve a different solubility of the peroxide or, upon mixing with the resin to be cured, within the resin.

All organic and inorganic peroxides so far known for being used in peroxide reactions such as the curing of unsaturated polyesters, can be used in the peroxide compositions according to the present invention. Most of these peroxides are commercially available. Preferably, the peroxide is selected from the group of acetylacetone peroxide, cyclohexanone peroxide, methylethylketone peroxide, dibenzoyl peroxide, alkylperoxides, all classes of hydroperoxides, percarbonates, perketals and inorganic peroxides. Apart from the ones already specifically mentioned before, examples of suitable peroxides are diacetyl peroxide, di-p-chlorobenzoyl peroxide, di-t-butyl peroxide, cumene hydroperoxide, phthaloyl peroxide, succinyl peroxide, dilauryl peroxide, acetylcyclohexanesulphonyl peroxide, t-butyl perbenzoate or t-butyl peroctoate, cyclohexane percarbonate, bis-(4-t-butylcyclohexyl) percarbonate, silicium peroxides, etc. Most preferred peroxides are the peroxides from the group of acetylacetone peroxide, cyclohexanone peroxide, methylethylketone peroxide and dibenzoyl peroxide.

The ratio between the amounts of peroxide and of diluent may be varied within a wide range and is not considered to be very critical. Usually the peroxide content in the peroxide composition according to the present invention will be chosen between 0.5 and 99, more preferably between 1.0 and 60, wt. % of the peroxide composition. The concentration range of the peroxides in the peroxide compositions according to the present invention is therefore not very critical in general. It is to be noticed, however, as the skilled man will be aware, that working with peroxides always should be done (starting with amounts of peroxide of less than 5 g per experiment) while taking appropriate safety precautions because of the strong tendency of such compounds to decompose exothermically. Some peroxides, for instance dibenzoyl peroxide, are known to be highly explosive when fully dissolved; for such types of peroxides suspensions or dispersions, or even completely solid blends of a peroxide and a suitable vinyl ether group(s) containing diluent, should be prepared instead of solutions.

The peroxides can easily be dissolved, completely or partially, in any of the vinyl ether monomers chosen in a concentration most suitable for the application and/or user's wishes. As will be mentioned further below, the concentration of the peroxide also can be adjusted in such manner that a peroxide dispersion or suspension is obtained. If solid blends of peroxides and a suitable vinyl ether group(s) containing diluent are to be prepared, this can easily be done by mixing particles of the peroxide with the grinded vinyl ether group(s) containing product.

The peroxide compositions according to the invention can be stored, without substantial loss of active peroxide content and without change in viscosity of their solutions, dispersions or suspensions, or without change in free-flowing behaviour for the solid blends, at ambient temperature for at least several weeks. During such storage, significant polymerization of the vinyl ether group(s) containing components could not be observed at all.

In a specifically preferred embodiment of the present invention, the viscosity (or free-flowing behaviour, as the case may be) of the peroxide compositions according to the invention can be adjusted by using as the diluent a mixture of (i) one or more vinyl ether monomer(s) and (ii) one or more vinyl ether oligo- or polymer(s). This leads to improvement in the flow and/or pumping behaviour. Adjusting said viscosity might also be particularly advantageous for improving the mixing behaviour of the peroxide compositions in the final application.

In fact, within the scope of the invention, it has been found possible that, instead of solutions of peroxides, suspensions of powdery or pasty peroxides (for example, of benzoyl peroxide) can be prepared, or free-flowing blends. It has been found, for instance, that suspensions of peroxides can conveniently be used on Resin Transfer Moulding (RTM) machines so that those RTM machines also can be operated at temperatures below 15° C. where, until the present invention, none of the known curing systems could be used with good results.

The peroxide compositions according to the invention, if so desired, also may comprise further additives for improving their behaviour during storage and/or in their final applications.

The present inventors, thus, now have succeeded in providing a new class of reactive diluents which enables the skilled man, who wishes to apply peroxides in chemical reactions, to apply the peroxide in any desired mixing ratio with the other chemical reactant(s). This will make it easy to adjust such mixing ratio according to the machine conditions and/or specific application methods used, without leading to impaired properties, such as mechanical resistance, and without leaving behind relatively high quantities of non-reacted materials in the finished part.

It is to be noticed that an almost 40 years old document, GB-A-915009, discloses that volatile monomers which are to be polymerised can also be used as a solvent for peroxides in such polymerisation reactions, provided that premature polymerisation of the monomer can be avoided and provided that the solution also contains 30 to 100 wt. % (calculated on the peroxide present) of a dissolved polymer or polycondensation product. Although this reference incidentally also mentions that, for instance, vinyl ethers such as vinyl butyl ether could be used as a solvent of peroxides, the document does not present any evidence that vinyl ethers indeed have been applied for such purpose in practice, nor that the phlegmatizing effects according to the present invention would occur.

The present invention further relates to the preparation of peroxide compositions comprising a reactive diluent. In the method for preparing peroxide compositions according to the present invention an organic or inorganic peroxide is blended either with a reactive diluent selected from the group of components. containing one or more vinyl ether group(s) and having a structure according to formula 1

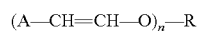

$(A-CH=CH-O)_n-R$         (formula 1), or is blended with a suitable resinous compound comprising, in a covalently built-in manner, a component containing one or more vinyl ether group(s). Further details as to the meaning of A, R and n, or as to the ways in which components with one or more vinyl ether group(s) are covalently built-in into a suitable resinous compound, have been described hereinbefore. As already has been described in the previous paragraphs, the peroxide compositions so prepared may be solutions, suspensions or dispersions, or even completely solid blends. The skilled man, taking into account all necessary safety precautions etc., can easily determine the most suitable combination of the components and their physical state.

The present invention also relates to the use of (a new class of) reactive diluents for peroxides in processes for radically curing of—optionally reinforced—unsaturated polyester resins for structural applications.

The (pumpable or free-flowing, as the case may be) peroxide compositions, whether in the form of solutions, suspensions or dispersions, or even completely solid blends according to the present invention are particularly suitable in the production of glass-fibre reinforced articles. For the production of such articles any suitable machinery known to the skilled man can be used. For instance, continuous laminating equipment and continuous filament winding machinery can suitably be used. In this type of equipment, mixing of the final resin preparation (by combining a peroxide composition and an uncured unsaturated polyester raw material) can be done in a delivery channel to the machine. Here relatively higher amounts of peroxide (especially in relatively high concentration in the reactive diluent) are advantageous for achieving the best possible mixing. In practice the upper limit to the concentration of the peroxide in the peroxide composition will be determined by the (desired) low content of phlegmatizer and/or unreacted diluent in the final products.

In spray-up applications usually higher amounts of peroxide composition can be used than in laminating applications, because in spray-up applications a better and more even peroxide distribution throughout the laminate can be obtained. In case higher amounts of peroxide (in the composition and/or the application) are used, curing results are more favourable, also because the fact that a homogeneous distribution of peroxide is achieved contributes to an even curing.

As mentioned above, it has been found that suspensions of peroxide compositions according to the invention can be used on Resin Transfer Moulding (RTM) machines so that those RTM machines also can be operated at temperatures even below 15° C.

The invention finally relates to products obtained by curing of, optionally reinforced, radically curable resins (unsaturated polyester resins, vinyl ester resins, vinyl urethane resins or mixtures thereof) with a peroxide composition according to the present invention. Initiated resin mixtures cured with peroxide mixtures in vinyl ethers show a faster gelling and curing behaviour as those initiated resin mixtures which were cured by an equal amount of the same peroxide without diluent.

The invention will now be illustrated by means of the following examples and comparative examples, which by no means are intended to limit the scope of the invention in any way:

Because working with peroxides always requires taking appropriate safety precautions, before performing the experiments reported below, first some preliminary experiments were done starting with amounts of peroxide of less than 5 g per experiment.

The following abbreviations are being used in the Tables for the peroxides tested:

| But M50 | Butanox M-50 | a standard, medium reactive methylethylketone peroxide |
|---|---|---|
| Trig 44B | Trigonox 44B | a fast cure acetylacetone peroxide |
| Trig HM | Trigonox HM | a methyl-iso-butylketone peroxide |
| Trig C | Trigonox C | a tert.butylperbenzoate |
| Cyc LR | Cyclonox LR | a low reactive cyclohexanone peroxide |
| Luci50 | Lucidol CH-50L | a dibenzoyl peroxide powder |
| Perk 16 | Perkadox 16 | a highly reactive percarbonate powder |
| Trig K80 | Trigonox K-80 | a cumyl hydroperoxide |
| Trig 21 | Trigonox 21 | a standard tert.butyl peroctoate |

EXAMPLES 1 AND 2; COMPARATIVE EXAMPLES A AND B

Comparison of Reactions for Peroxide Compositions with Vinyl Ethers with (Comparative) Reactions for Phlegmatized Peroxide Compositions According to the State-Of-The-Art All experiments for testing the curing behaviour were carried out with a Palatal P 6-01 resin (an unsaturated, highly reactive, polyester resin of DSM Composite Resins, dissolved in 35 wt. % of styrene) from the same production batch. For the curing Trigonox 44B (an acetylacetone peroxide) and Butanox M 50 (a methylethylketone peroxide) were used, as are available from Akzo Nobel. The curing of the resin was accelerated by the addition of 0.5 wt. % Accelerator NL 49 P (a product of Akzo Nobel, being a 1% solution of cobalt octoate in a phthalate solvent), calculated as wt. % in relation to the dry solid resin content of Palatal P 6-01.

Gel times (associated with the interval 25° C.–35° C.), and cure times (associated with the interval from 25° C. to reaching of the exothermal peak, as indicated in ° C.) were measured, in minutes, using techniques according to DIN 16945, at 25° C. in a thermostatted bath, respectively in a well defined test tube.

|  | Comparative Example A | Example 1 |
|---|---|---|
| Cured with | 1% Trig 44B | 2% Trig 44B/HBUVE 1:1 |
| 25° C.–35° C. (min.) | 14.1 | 11.3 |

-continued

| 25° C.–peak temp. (min.) | 18.4 | 15.5 |
|---|---|---|
| Peak temperature (° C.) | 177 | 175 |

|  | Comparative Example B | Example 2 |
|---|---|---|
| Cured with | 1% But M50 | 2% But M50/HBUVE 1:1 |
| 25° C.–35 ° C. (min.) | 13.9 | 9.3 |
| 25° C.–peak temp. (min.) | 23.2 | 17.3 |
| Peak temperature (° C.) | 166 | 164 |

The peroxide/vinyl ether mixtures (according to the examples and comparative examples) were stored for respectively 14, and 50 days at room temperature. The curing experiments were repeated, using the same type and amount of accelerator.

Repeat of the experiments after 14 days' storage:

|  | Comp. Ex. A Trigonox 44B | Example 1 Trigonox 44B/ HBUVE | Comp. Ex. B Butanox M50 | Example 2 Butanox M50/ HBUVE |
|---|---|---|---|---|
| 25–35° C. (min.) | 15.1 | 10.4 | 16.2 | 23.1 |
| 25° C.–$T_{peak}$ (min.) | 19.4 | 14.5 | 27.1 | 36.2 |
| $T_{peak}$ (° C.) | 175 | 175 | 160 | 145 |

Repeat of the experiments after 50 days' storage:

|  | Comp. Ex. A Trigonox 44B | Example 1 Trigonox 44B/ HBUVE | Comp. Ex. B Butanox M50 | Example 2 Butanox M50/ HBUVE |
|---|---|---|---|---|
| 25–35° C. (min.) | 15.3 | 12.5 | 16.5 | 45.0 |
| 25° C.–$T_{peak}$ (min.) | 20.0 | 17.5 | 28.0 | Stopped at 64.0 |
| $T_{peak}$ (° C.) | 175 | 169 | 158 | — |

It is clear from these results, that peroxides can be diluted suitably, up to about 50%, by blending with a vinyl ether component, and that the compositions obtained can be stored for at least 50 days, without loosing reactivity. Moreover, it can be seen that after 50 days' storage faster curing is obtained in the presence of the vinyl ether diluent than in absence thereof.

EXAMPLE 3

Stability Tests

In Example 3, summarized in the following Table, a series of commercially available peroxides (all from Akzo Nobel; as indicated) has been mixed in a 250 ml beaker with equal amounts (by weight) of HBUVE. The mixtures so prepared were stored for 3 months, and the stability of the peroxides was tested, respectively after 1 week, 4 weeks, 2 months and 3 months. Observations made (immediately upon the mixing, and in the course of keeping the mixtures) are summarized in the Table. In none of the mixing experiments gassing or substantial changes of the composition occurred.

The results of Example 3 show, that very many peroxides can suitably be diluted by vinyl ether group(s) containing components without occurrence of substantial reaction of the peroxides. According to the invention, vinyl ether group(s) containing compounds are suitable diluents for peroxides.

TABLE AD EXAMPLE 3

| Peroxide | Reaction at mixing With HBUVE | Observations at Mixing | Stability tests for 3 months |
|---|---|---|---|
| But M50 | None, no heat up | Clear, stable | Stable |
| Trig 44B | None, no heat up | Clear, stable | Stable |
| Trig HM | None, no heat up | Clear, stable | Stable |
| Trig C | Red coloration | Clear, slightly pink, stable | Stable, slightly pink |
| Cyc LR | None | Clear, stable | Stable |
| Luci50 | None | White suspension | Stable, white suspension |
| Perk 16 | None | White creamy mixt., after 2 h at RT gelled | Not tested |
| Trig K80 | Red coloration | Clear, slight pink, stable | Stable (only tested 4 weeks) |
| Trig 21 | None | Clear, stable | Stable |

The invention claimed is:

1. Peroxide compositions comprising a reactive diluent for the peroxide, wherein the diluent, itself being a phlegmatizer, is either a component containing one or more vinyl ether group(s) and having a (monomeric) structure according to formula 1

(A—CH=CH—O)$_n$—R     (formula 1)

where
A represents hydrogen or an alkyl group with 1–3 C atoms, and where, if there is more than one A, the individual A groups may be the same or different
R either represents an aliphatic group, optionally branched, with 1–20 C atoms, which may also contain a cyclohexyl or a 1,4-dimethylenecyclohexyl group and in the carbon chain optionally also one or more O and/or S atoms, which group may be substituted with one or more functional group(s) chosen from either a hydroxyl group or an amino group, optionally substituted with one or two alkyl groups with 1–3 C atoms, n is 1, 2, 3 or 4
or is a suitable resinous compound comprising, in a covalently built-in manner, a component containing one or more vinyl ether group(s), wherein the composition includes no further co-polymerizable material.

2. Peroxide compositions according to claim 1, wherein the monomeric component containing one or more vinyl ether group(s) is selected from the group of mono-or divinyl ether monomers.

3. Peroxide compositions according to claim 2, wherein the component containing one or more vinyl ether group(s) is hydroxybutyl vinyl ether (HBUVE), diethyleneglycol divinyl ether (DEODVE) or triethyleneglycol divinyl ether (TEGDVE).

4. Peroxide compositions according to claim 1, wherein the peroxide is selected from the group of acetylacetone peroxide, cyclohexanone peroxide, methylethylketone peroxide, dibenzoyl peroxide, alkylperoxides, hydroperoxides, percarbonates, perketals and inorganic peroxides.

5. Peroxide compositions according to claim 4, wherein the peroxide is acetylacetone peroxide, cyclohexanone peroxide, methylethylketone peroxide, or dibenzoyl peroxide.

6. Peroxide compositions according to claim 1, wherein the ratio between the amounts of peroxide and of diluent are chosen so that the content of peroxide in the composition is in the range of between 0.5 and 99, preferably between 1.0 and 60 wt. % of the peroxide composition.

7. Method for preparing peroxide compositions comprising a reactive diluent for the peroxide, wherein an organic or inorganic peroxide is blended either with a reactive diluent, itself being a phlegmatizer, selected from the group of components containing one or more vinyl ether group(s) and having a structure according to formula 1

(A—CH=CH—O)$_n$—R     (formula 1)

or is blended with a suitable resinous compound comprising, in a covalently built-in manner, a component containing one or more vinyl ether group(s) as is obtained by reaction of a mixture of appropriate amounts of
a) a first compound (the HVE-compound) containing at least one hydroxyl group and at least one vinyl ether group, and
b) a second compound (the D/HIC-compound), being a diisocyanate or higher isocyanate, reacting with formation of one or more urethane group(s), and
c) a third compound (the G/P/HP-compound) chosen from the groups of (1) $C_{2-6}$ glycols, (2) $C_{5-20}$ polyols having 2–5 hydroxyl groups and (3) saturated or (ethylenically) unsaturated hydroxyl terminated polyester compounds, not being alkyd resins, having 1–5 free hydroxyl groups and from 2–50 monomeric ester units (the G/P/HP-compound), or mixtures thereof,
wherein the peroxide compositions include no further co-polymerizable material.

8. A product obtained by curing with a peroxide composition according to claim 1.

9. A product obtained from the method of claim 7.

10. A method for curing a radically curable resin comprising curing the resin in the presence of a peroxide composition according to claim 1.

11. Peroxide compositions according to claim 1, wherein the composition is in the form of a solution.

12. Peroxide compositions according to claim 1, wherein the composition is in the form of a suspension.

13. Peroxide compositions according to claim 1, wherein the composition is in the form of a solid.

14. Peroxide compositions according to claim 13, wherein the composition is in the form of a free-flowing powder.

* * * * *